United States Patent
Fell et al.

(10) Patent No.: US 10,548,782 B2
(45) Date of Patent: *Feb. 4, 2020

(54) METHOD OF FORMING AN ABSORBENT STRUCTURE

(71) Applicant: Kimberly-Clark Worldwide, Inc., Neenah, WI (US)

(72) Inventors: David Arthur Fell, Neenah, WI (US); Steven Michael Hurley, Neenah, WI (US); Donald LeRoy Smith, Tyler, TX (US); Kendell Jean Williams, Greenville, WI (US); Nicholas Alan Kraft, Matthews, NC (US); Johanna Marie Buss, Appleton, WI (US); David John Paulson, Appleton, WI (US); Thomas Gerard Vercauteren, Appleton, WI (US); Sara Lynn Rosack, Appleton, WI (US); James George Van Himbergen, Kimberly, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 240 days.

This patent is subject to a terminal disclaimer.

(21) Appl. No.: 15/723,323

(22) Filed: Oct. 3, 2017

(65) Prior Publication Data

US 2018/0021188 A1 Jan. 25, 2018

Related U.S. Application Data

(60) Continuation of application No. 15/399,100, filed on Jan. 5, 2017, now Pat. No. 9,808,381, which is a (Continued)

(51) Int. Cl.
*A61F 13/538* (2006.01)
*A61F 13/531* (2006.01)
(Continued)

(52) U.S. Cl.
CPC ...... *A61F 13/538* (2013.01); *A61F 13/00991* (2013.01); *A61F 13/15626* (2013.01);
(Continued)

(58) Field of Classification Search
None
See application file for complete search history.

(56) References Cited

U.S. PATENT DOCUMENTS

| 4,348,251 A | 9/1982 | Pauls et al. |
| 5,064,689 A | 11/1991 | Young, Sr. et al. |

(Continued)

FOREIGN PATENT DOCUMENTS

| CN | 1520278 A | 8/2004 |
| CN | 201244131 Y | 5/2009 |

(Continued)

*Primary Examiner* — Mary Lynn F Theisen
(74) *Attorney, Agent, or Firm* — Kimberly-Clark Worldwide, Inc.

(57) ABSTRACT

A liquid absorbent structure is made by dry laying a fibrous web having incorporated therein a superabsorbent material, and applying an aqueous composite stabilizer to at least one surface of the web. The aqueous composite stabilizer imparts integrity to the resulting structure without substantially impairing the effectiveness of the superabsorbent material to absorb liquid while forming the absorbent structure without removing the water from aqueous composite stabilizer or drying out the absorbent structure. The absorbent composite absorbs the water from the aqueous composite stabilizer. The absorbent composite comprises about 70% by weight of a superabsorbent material.

13 Claims, 8 Drawing Sheets

Related U.S. Application Data division of application No. 14/186,305, filed on Feb. 21, 2014, now Pat. No. 9,572,729.

(60) Provisional application No. 61/884,184, filed on Sep. 30, 2013.

(51) Int. Cl.

| | | |
|---|---|---|
| *A61F 13/15* | (2006.01) | |
| *A61F 13/53* | (2006.01) | |
| *A61F 13/00* | (2006.01) | |
| *B32B 27/06* | (2006.01) | |
| *B32B 27/32* | (2006.01) | |

(52) U.S. Cl.
CPC .......... *A61F 13/531* (2013.01); *B32B 27/065* (2013.01); *B32B 27/32* (2013.01); *A61F 2013/15926* (2013.01); *A61F 2013/530489* (2013.01); *A61F 2013/530635* (2013.01); *B32B 2555/02* (2013.01)

(56) References Cited

U.S. PATENT DOCUMENTS

| | | |
|---|---|---|
| 5,128,082 A | 7/1992 | Makoui |
| 5,230,959 A | 7/1993 | Young, Sr. et al. |
| 5,308,896 A | 5/1994 | Hansen et al. |
| 5,352,480 A | 10/1994 | Hansen et al. |
| 5,378,528 A | 1/1995 | Makoui |
| 5,422,169 A | 6/1995 | Roe |
| 5,429,788 A | 7/1995 | Ribble et al. |
| 5,538,783 A | 7/1996 | Hansen et al. |
| 5,543,215 A | 8/1996 | Hansen et al. |
| 5,859,074 A | 1/1999 | Rezai et al. |
| 5,938,648 A | 8/1999 | Beck et al. |
| 5,961,763 A | 10/1999 | Makoui et al. |
| 6,060,115 A | 5/2000 | Borowski et al. |
| 6,270,893 B1 | 8/2001 | Young, Sr. et al. |
| 6,391,453 B1 | 5/2002 | Hansen et al. |
| 6,403,857 B1 | 6/2002 | Gross et al. |
| 6,425,979 B1 | 7/2002 | Hansen et al. |
| 6,461,553 B1 | 10/2002 | Hansen et al. |
| 6,533,989 B1 | 3/2003 | Wisneski et al. |
| 6,596,103 B1 | 7/2003 | Hansen et al. |
| 6,603,054 B2 | 8/2003 | Chen et al. |
| 6,608,237 B1 | 8/2003 | Li et al. |
| 7,138,561 B2 | 11/2006 | Fuchs et al. |
| 7,786,341 B2 | 8/2010 | Schneider et al. |
| 8,017,827 B2 | 9/2011 | Hundorf et al. |
| 8,148,598 B2 | 4/2012 | Tsang et al. |
| 2002/0013560 A1 | 1/2002 | Erspamer et al. |
| 2003/0070780 A1 | 4/2003 | Chen et al. |
| 2004/0220539 A1 | 11/2004 | Glaug et al. |
| 2005/0148964 A1 | 7/2005 | Chambers, Jr. et al. |
| 2006/0004335 A1 | 1/2006 | Wang et al. |
| 2006/0155254 A1 | 7/2006 | Sanz et al. |
| 2008/0312625 A1 | 12/2008 | Hundorf et al. |
| 2009/0270825 A1 | 10/2009 | Wciorka et al. |
| 2010/0051166 A1 | 3/2010 | Hundorf et al. |
| 2010/0071847 A1 | 3/2010 | Shin et al. |
| 2010/0071848 A1 | 3/2010 | Verstegen et al. |
| 2011/0184365 A1 | 7/2011 | Roettger et al. |
| 2012/0004632 A1 | 1/2012 | Zhang et al. |
| 2012/0071847 A1 | 3/2012 | Bewick-Sonntag et al. |
| 2012/0071848 A1 | 3/2012 | Zhang et al. |
| 2012/0231946 A1 | 9/2012 | Goda et al. |

FOREIGN PATENT DOCUMENTS

| | | |
|---|---|---|
| CN | 102333551 A | 1/2012 |
| CN | 102548654 A | 7/2012 |
| EP | 1 260 626 A2 | 11/2002 |
| EP | 1 260 627 A2 | 11/2002 |
| WO | WO 2001/035886 A1 | 5/2001 |

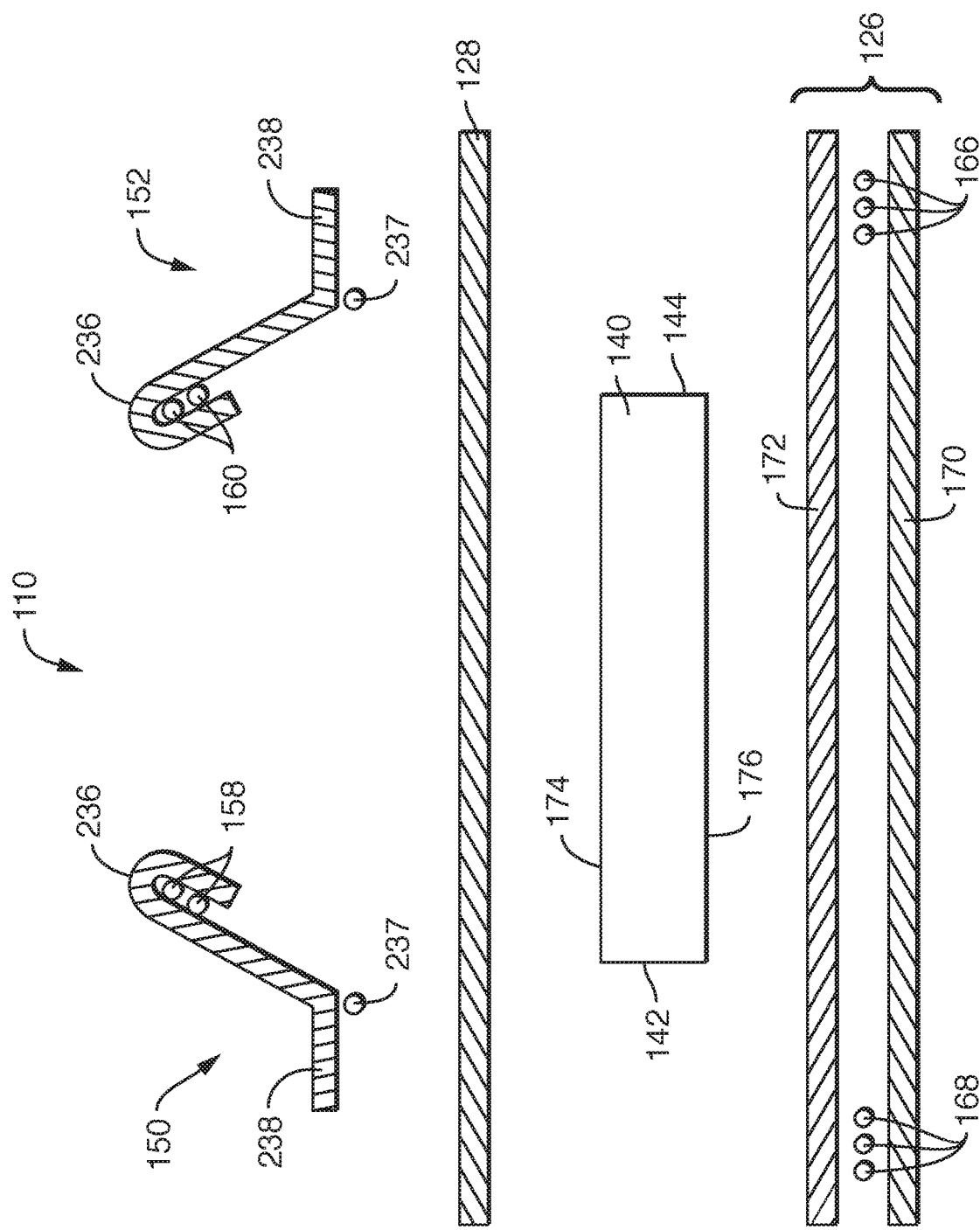

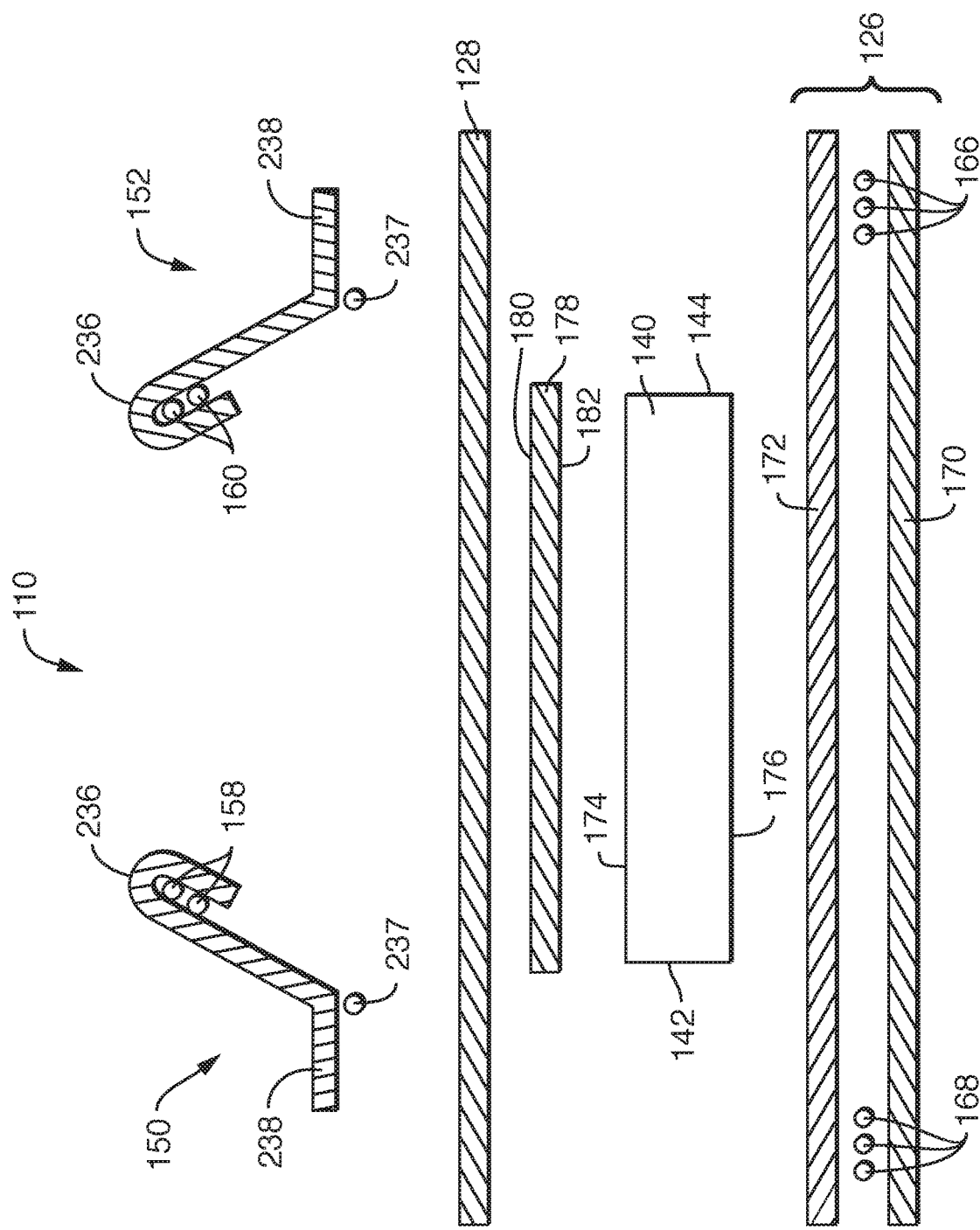

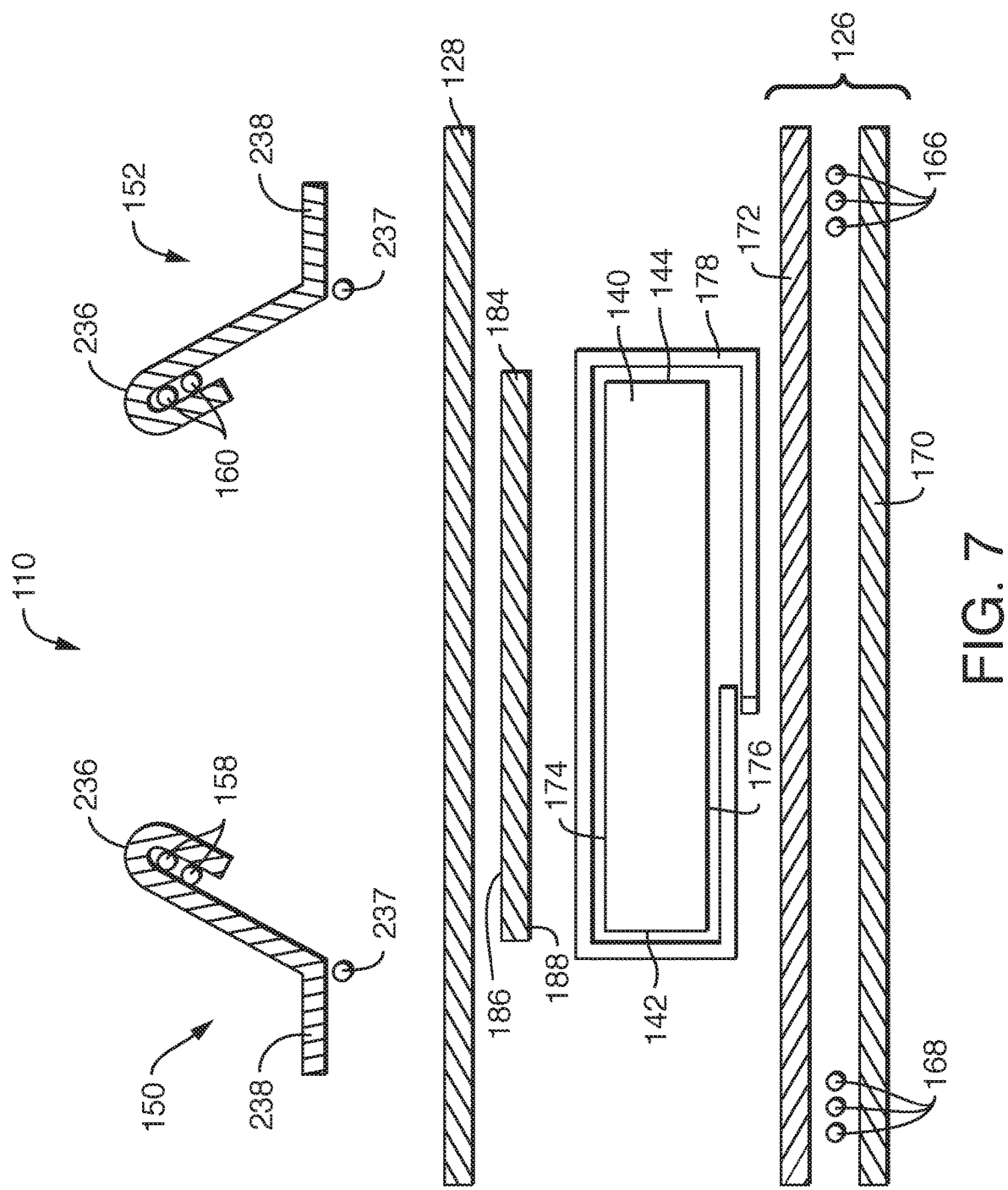

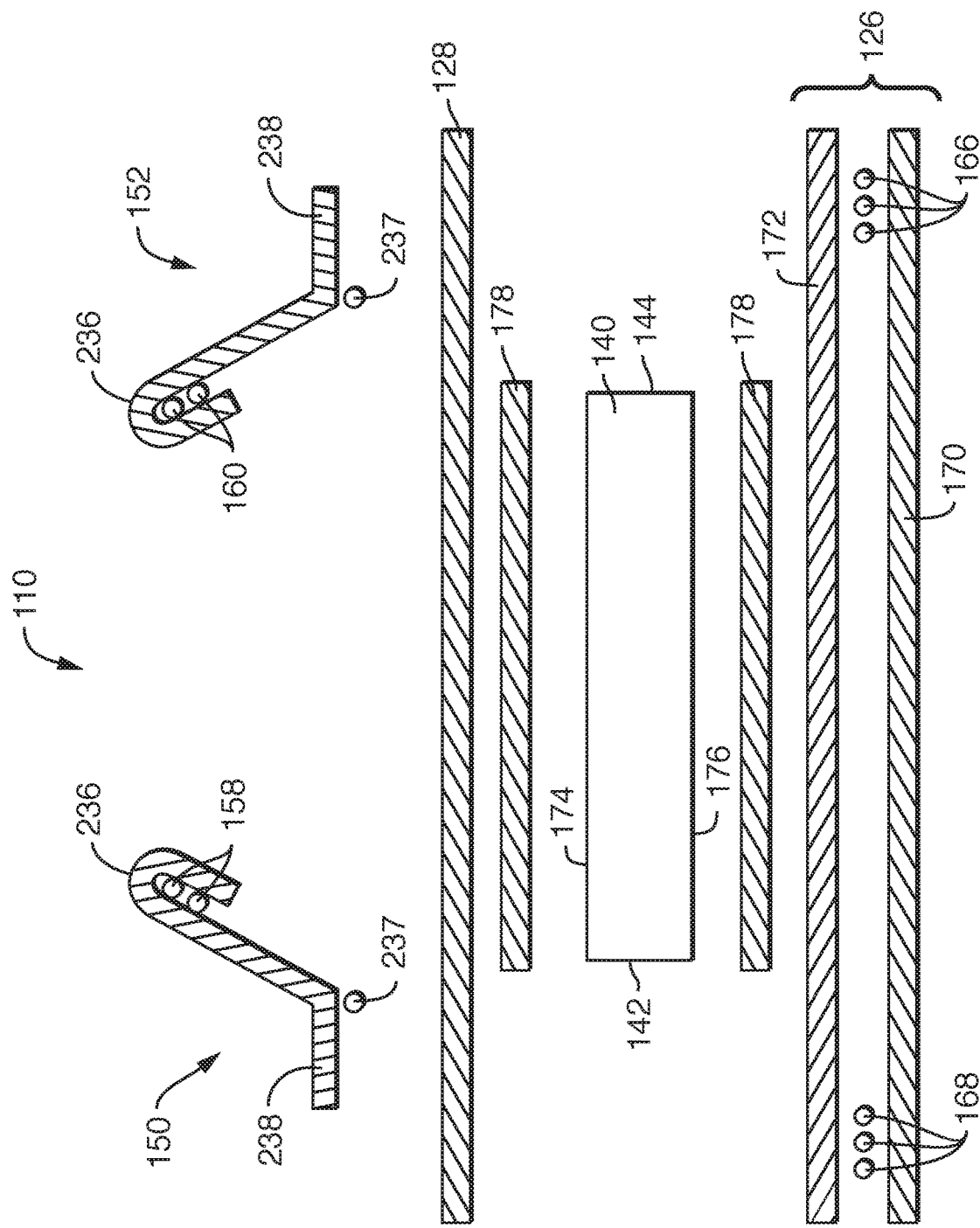

METHOD OF FORMING AN ABSORBENT STRUCTURE

The present application is a Continuation Application of and claims priority to U.S. patent application Ser. No. 15/399,100, entitled "Method of Forming an Absorbent Structure" and filed on Jan. 5, 2017, which is a Divisional Application of and claims priority to U.S. Pat. No. 9,572,729, entitled "Method of Forming An Absorbent Structure" and filed on Feb. 21, 2014, which claims priority to U.S. Provisional Application No. 61/884,184, entitled "Method of Forming An Absorbent Structure" and filed on Sep. 30, 2013, the contents of which are hereby incorporated by reference in a manner consistent with the present application.

BACKGROUND

Absorbent composites containing high levels of superabsorbent polymer exhibit increased problems maintaining composite integrity. This is due to insufficient fiber to contain and restrict the mobility and migration of superabsorbent material in the composite. This is a problematic situation, since there is a very strong motivation to design and produce thin, flexible, comfortable absorbent products. The lack of integrity in an absorbent composite also challenges the ability to manufacture products with high superabsorbent material composites at fast line speeds. In addition, upon initial product use, migration of the superabsorbent material in the product can compromise fluid performance and product comfort during extended use including issues such as sagging and drooping.

In addition, with more mobile superabsorbent material, gel on skin can become an increased problem that needs to be avoided. Integrity has been improved at higher superabsorbent material via either an embossing pattern on the composite or debulking the composite or using hot melt adhesives. However, embossing or debulking damages the superabsorbent, compromising fluid properties of the absorbent product.

Therefore, a method of forming a soft, absorbent structure that exhibits high integrity and relatively low bulk is needed.

SUMMARY

Generally, a method of forming an absorbent structure for use in an absorbent article is disclosed herein. The method includes providing a core forming surface, forming an absorbent composite on the core forming surface, applying an aqueous composite stabilizer containing a stabilizing component and water to stabilize the absorbent structure. Forming the absorbent structure is completed without removing the water from aqueous composite stabilizer or drying out the absorbent structure. The superabsorbent in the absorbent composite absorbs the water from the aqueous composite stabilizer. The absorbent composite comprises about 70% by weight of a superabsorbent material. It is important for the absorbent composite to have a high level of superabsorbent materials since it eliminates a lot of the quality control issues associated with not having a drying step such as molding or other issues.

Controlling the amount of the stabilizing component in the aqueous composite stabilizer is important to maintain proper functioning of the absorbent composite and to maintain integrity of the material. In an embodiment, the stabilizing component is applied at an add-on rate of between about 1% and about 4% by weight of the absorbent structure. In desirable embodiment, the stabilizing component is applied at an add-on rate of between about 1.5% and about 2.5% by weight of the absorbent structure.

In an embodiment, the aqueous composite stabilizer contains a dissolved or suspended stabilizing component which comprised vinyl acetate and acrylic ester copolymers, vinyl acetate ethylene copolymers, vinyl acetate ethylene acrylate copolymers, styrene butadiene carboxylate copolymers, polyacrylonitriles, and combinations thereof. In an embodiment, the aqueous composite stabilizer contains from about 7.5% to about 55% by weight of the stabilizing component and from about 45% to about 92.5% by weight water. In another embodiment, the aqueous composite stabilizer contains from about 7.5% to about 25% by weight of the stabilizing component. In a desirable embodiment, the aqueous composite stabilizer contains from about 11.5% to about 15.5% by weight of the stabilizing component.

DESCRIPTION OF THE DRAWINGS

FIG. 5 is an exploded cross-sectional view of an embodiment of an absorbent article.

FIG. 6 is an exploded cross-sectional view of another embodiment of an absorbent article.

FIG. 7 is an exploded cross-sectional view of another embodiment of an absorbent article.

FIG. 8 is an exploded cross-sectional view of another embodiment of an absorbent article.

DEFINITIONS

Figure 1:
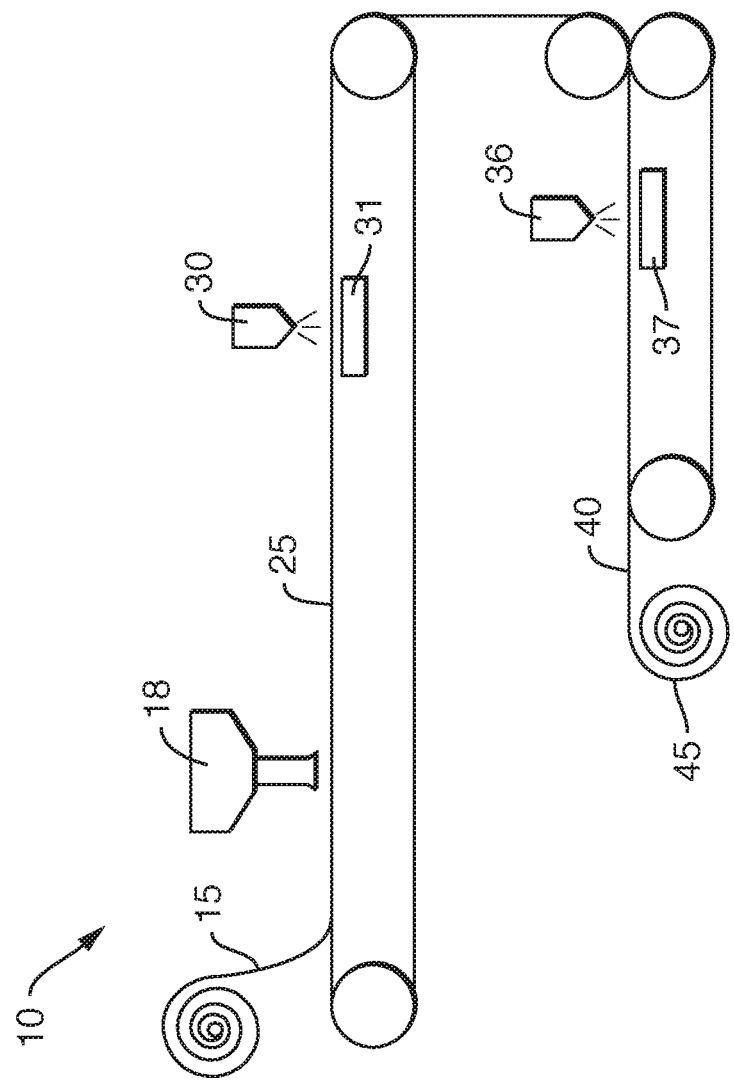
FIG. 1 is a schematic side view of an embodiment of an apparatus and a process for forming an absorbent structure.

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, feminine hygiene products, including, but not limited to, menstrual pads, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements.

The term "carded web" refers herein to a web containing natural or synthetic staple fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "g/cc" refers herein to grams per cubic centimeter.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 degrees are designated "wettable" or hydrophilic, and fibers having contact angles greater than 90 degrees are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a polymeric material which becomes pliable or moldable above a specific temperature and returns to a solid state upon cooling.

DETAILED DESCRIPTION

Generally, a method of forming an absorbent structure for use in an absorbent article is disclosed herein. The method includes providing a core forming surface, forming an absorbent composite on the core forming surface, applying an aqueous composite stabilizer containing a stabilizing component and water to stabilize the absorbent structure. Forming the absorbent structure is completed without removing the water from aqueous composite stabilizer or drying out the absorbent structure. The superabsorbent in the absorbent composite absorbs the water from the aqueous composite stabilizer. The absorbent composite comprises about 70% by weight of a superabsorbent material.

Figure 2:
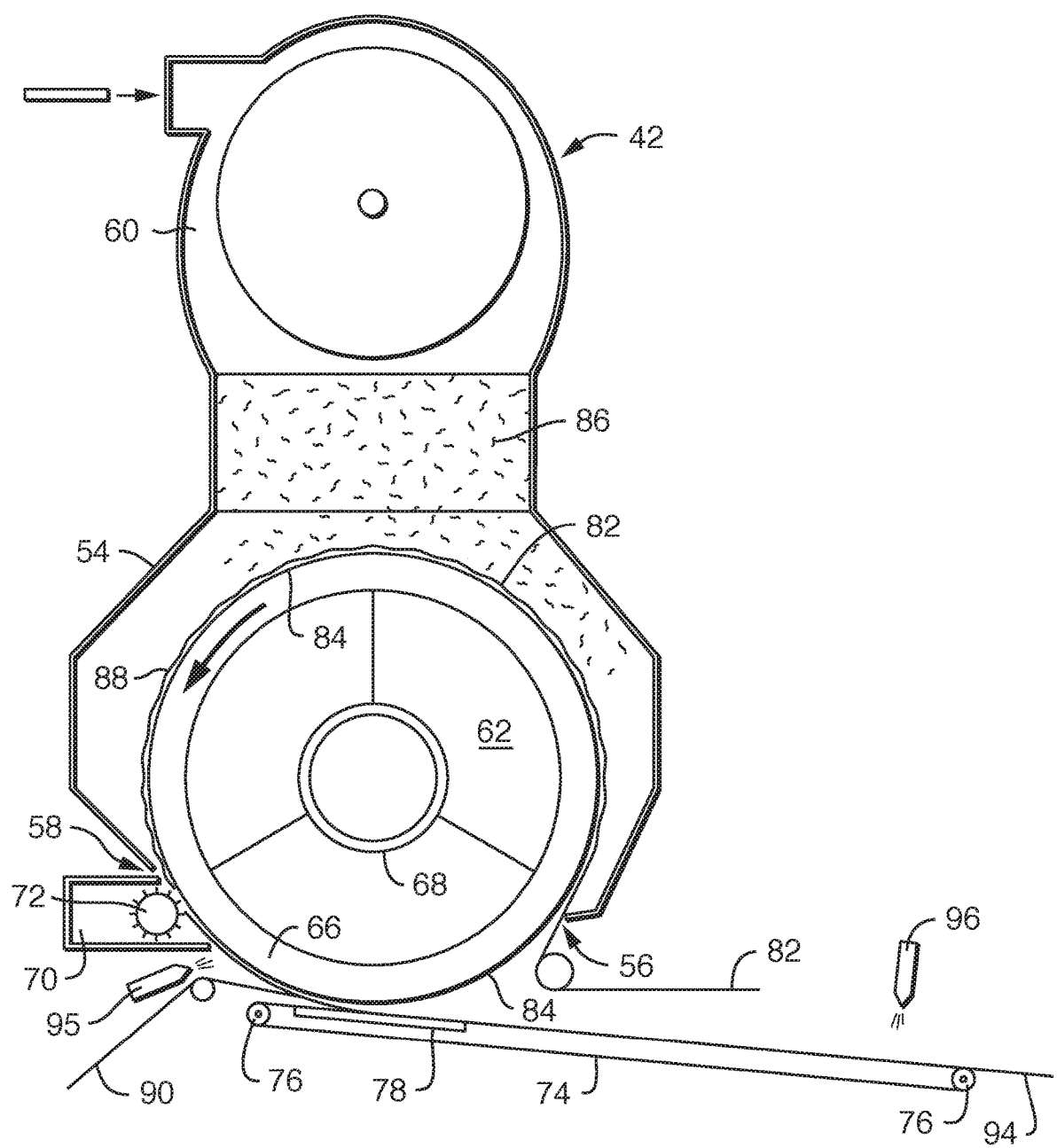
FIG. 2 is a schematic side view of another embodiment of an apparatus and a process for forming an absorbent structure.

FIG. 1 illustrates an embodiment of a system 10 of manufacture of the absorbent structure of the invention described herein. A forming surface 15 may be a substrate such as a core wrap layer described in more detail below. Alternatively, the forming surface 15 can be one or more forming chambers that include rotatable, vacuum-forming drums. Optionally, the multiple forming chambers can include combinations of flat-wire forming surfaces and rotatable drum forming surfaces. For example, FIG. 2 illustrates a forming chamber formed using a vacuum forming drum. Desirably, the vacuum is set between about 1 to about 50 inches of water.

An absorbent composite 25 may be deposited onto the forming surface 15 via a distributor unit 18. In an embodiment, the absorbent composite 25 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In a desirable embodiment, the absorbent composite 25 can be a matrix of cellulosic fluff and superabsorbent material.

In an embodiment, the absorbent composite 25 may be constructed of a single layer of materials, or in the alternative, may be constructed of two layers of materials or more. In one embodiment, the absorbent composite 25 may be homogenous matrix of cellulosic pulp fluff and superabsorbent material. In an embodiment in which the absorbent composite 25 has two layers, the absorbent composite 25 can have a wearer facing layer suitably composed of hydrophilic fibers and a garment facing layer suitably composed at least in part of a high absorbency material commonly known as superabsorbent material. In such an embodiment, the wearer facing layer of the absorbent composite 25 can be suitably composed of cellulosic fluff, such as wood pulp fluff, and the garment facing layer of the absorbent composite 40 can be suitably composed of superabsorbent material, or a mixture of cellulosic fluff and superabsorbent material. As a result, the wearer facing layer can have a lower absorbent capacity per unit weight than the garment facing layer. The wearer facing layer may alternatively be composed of a mixture of hydrophilic fibers and superabsorbent material. It is also contemplated that the garment facing layer may be composed solely of superabsorbent material without departing from the scope of this disclosure. It is also contemplated that, in an embodiment, each of the layers, the wearer facing and garment facing layers, can have a superabsorbent material such that the absorbent capacities of the two superabsorbent materials can be different and can provide the absorbent composite 25 with a different absorbent capacity in the wearer facing layer than in the garment facing layer.

Various types of wettable, hydrophilic fibers can be used in the absorbent composite 25. Examples of suitable fibers include natural fibers; cellulosic fibers; crosslinked cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been surface rendered hydrophilic by suitable means. The fibers may be surface rendered hydrophilic, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. For example, one suitable type of fiber is a wood pulp that is a bleached, highly absorbent sulfate wood pulp containing primarily soft wood fibers. However, the wood pulp can be exchanged with other fiber materials, such as synthetic, polymeric, or meltblown fibers or with a combination of meltblown and natural fibers. In an embodiment, the cellulosic fluff can include a blend of wood pulp fluff.

The absorbent composite 25 can be formed with a dry-forming technique, an air-forming technique, or the like, as well as combinations thereof. Methods and apparatus for carrying out such techniques are well known in the art.

Suitable superabsorbent materials can be selected from natural, synthetic, and modified natural polymers and materials. The superabsorbent materials can be inorganic materials, such as silica gels, or organic compounds, such as cross-linked polymers. Cross-linking may be covalent, ionic, Van der Waals, or hydrogen bonding. Typically, a superabsorbent material can be capable of absorbing at least about ten times its weight of an aqueous liquid. In an embodiment, the superabsorbent material can absorb more than forty times its weight in liquid. Examples of superabsorbent materials include polyacrylamides, polyvinyl alcohol, ethylene maleic anhydride copolymers, polyvinyl ethers, hydroxypropyl cellulose, carboxymal methyl cellulose, polyvinylmorpholinone, polymers and copolymers of vinyl sulfonic acid, polyacrylates, polyacrylamides, polyvinyl pyrrolidone, and the like. Additional polymers suitable for superabsorbent material include hydrolyzed, acrylonitrile grafted starch, acrylic acid grafted starch, polyacrylates and isobutylene maleic anhydride copolymers and mixtures thereof. The superabsorbent material may be in the form of discrete particles. The discrete particles can be of any desired shape, for example, spiral or semi-spiral, cubic, rod-like, polyhedral, etc. Shapes having a largest greatest dimension/smallest dimension ratio, such as needles, flakes, and fibers are also contemplated for use herein. Conglomerates of particles of superabsorbent materials may also be used in the absorbent composite 25.

In an embodiment, the absorbent composite 25 can have at least about 70% by weight of a superabsorbent material. In an embodiment, the absorbent composite 25 can have at least about 70 to about 100% by weight of a superabsorbent material. Examples of superabsorbent material include, but are not limited to, FAVOR SXM-9500 or equivalent available from Evonik Industries, Greensboro, N.C., U.S.A. and HYSORB 8760 or equivalent available from BASF Corporation, Charlotte, N.C., U.S.A. Typically, the absorbent composite has a basis weight of between 200 and 1000 grams per square meter.

At this stage of the process, the absorbent composite 25 has very little integrity and requires stabilization. The absorbent composite 25 is advanced by the forming surface 15, and where desired, the absorbent composite 25 first may be passed by a suitable dispensing means 30, such as a spray nozzle, doctor blade, roller applicator, or the like, where an aqueous composite stabilizer is applied to the surface of the loose web. A vacuum applied by suction box 31 positioned beneath the dispensing means 30 helps to draw the absorbent composite stabilizer into the absorbent composite 25. The dispensing means or applicator is essentially coextensive with the width of the absorbent composite 25, and preferably a substantially uniform coating of the aqueous composite stabilizer is applied to the absorbent composite. However, the aqueous composite stabilizer may be applied as a non-uniform, random or pattern coating, and because the aqueous composite stabilizer is water-based, it will diffuse throughout the absorbent composite 25 and function as a binder. The extent or degree of penetration of the aqueous composite stabilizer into the absorbent composite 25 is controlled by controlling the amount of aqueous composite stabilizer applied and by controlling the vacuum applied to the web in that the vacuum helps to draw the aqueous composite stabilizer into the web. The aqueous composite stabilizer is usually applied as an aqueous emulsion. It is optional to coat both surfaces of the absorbent composite with the aqueous composite stabilizer, and this is readily accomplished by reverse rolling the web so that the top surface at the dispensing means 30 becomes the bottom surface. Thus, the absorbent composite 25 is advanced to a second dispensing means 36, including suction box 37, where aqueous composite stabilizer is now applied to the opposite side forming a resultant absorbent structure 40. Other configurations for applying the aqueous composite stabilizer to both sides of the absorbent composite can be used by a person skilled in the art.

If using a core wrap layer as the forming surface 15, once the absorbent composite 25 is deposited on the surface, the core wrap layer may be folded over on itself and then sealed using, for example, heat, hot melt adhesive and/or pressure. Alternatively, a core wrap layer may be composed of separate sheets of material which can be utilized to partially or fully encompass the absorbent composite and which can be sealed together using a sealing means such as an ultrasonic bonder or other thermochemical bonding means or the use of an adhesive. The aqueous composite stabilizer may be sprayed onto the core wrap layer or directly on the absorbent composite web.

In an embodiment, the aqueous composite stabilizer contains dissolved or suspended stabilizing component. The stabilizing component may comprise vinyl acetate and acrylic ester copolymers, vinyl acetate ethylene copolymers, vinyl acetate ethylene acrylate copolymers, styrene butadiene carboxylate copolymers, and polyacrylonitriles. In an embodiment, the aqueous composite stabilizer contains from about 7.5% to about 55% by weight of the stabilizing component and from about 45% to about 92.5% by weight water. In another embodiment, the aqueous composite stabilizer contains from about 7.5% to about 25% by weight of the stabilizing component. In a desirable embodiment, the aqueous composite stabilizer contains from about 11.5% to about 15.5% by weight of the stabilizing component. Suitable copolymers for use in the aqueous composite stabilizer include VINNAPAS® EZ 123, VINNAPAS® EAF 68, VINNAPAS® 920, VINNAPAS® EF 539, VINNAPAS® EF 101, or equivalent commercially available from Wacker Chemie AG, Munich, DE. Other suitable dispersions may include Cariflex IR 0401 or equivalent commercially available from Kraton Polymers U.S. LLC, Houston, Tex., U.S.A.

As discussed above, controlling the amount of the stabilizing component in the aqueous composite stabilizer is important to maintain proper functioning of the absorbent composite 25 and to maintain integrity of the material. In an embodiment, the stabilizing component is applied at an add-on rate of between about 1% and about 4% by weight of the absorbent composite. In desirable embodiment, the stabilizing component is applied at an add-on rate of between about 1.5% and about 2.5% by weight of the absorbent composite.

The resulting absorbent structure 40 exhibits sufficient integrity so that it can be cut, rolled, or incorporated into an absorbent article while it is still wet. In another embodiment, the absorbent structure is not cured to impart integrity to the structure. As shown, the absorbent structure 40 is taken up on roller 45, and may be used as stock for a finished product such as of the type described below in detail. Alternatively, the absorbent structure 40 may be incorporated into the finished product directly.

Another embodiment of a system 42 of manufacture for forming an absorbent structure is illustrated in FIG. 2. The system 42 of manufacture shown in FIG. 2 is a conventional airforming apparatus, the operation and construction of which is known to those skilled in the art. It also understood that the web of absorbent composite may be made other than by airforming apparatus, such as by airlaying apparatus, coforming apparatus or other suitable forming apparatus and remain within the scope of this invention The system 42 of manufacture includes conforming a first web 82 onto a forming surface 84, depositing absorbent material 86 onto the first web 82 to form a unitary absorbent composite 88, and joining a second web 90 in facing relation with the first web 82 to form an absorbent structure 94 wherein the absorbent composite 88 is located between the first web 82 and the second web 90.

The system 42 and apparatus of the invention can include a forming chamber 54 through which the forming surface 84 is movable. The forming chamber 54 has an appointed entrance portion 56, and an appointed exit portion 58. A fiber source, such as provided by a fiberizer 60, can be configured to provide fibrous material into the forming chamber 54, and a vacuum generator or other vacuum source can be configured to provide an operative, relatively lower pressure, vacuum condition in a vacuum-commutator duct system 62. In the illustrated configuration, the fiberizer 60 can be provided by a rotary hammer mill or a rotatable picker roll. Other fiberizers may also be employed, as desired. Other component materials for producing the absorbent composite 88 may also be delivered into the forming chamber 54. For example, particles or fibers of superabsorbent material are also introduced into the forming chamber 54 by employing conventional mechanisms, such as pipes, channels, spreaders, nozzles, and the like, as well as combinations thereof. In the representatively shown configuration, the superabsorbent material can be delivered into the forming chamber 54. The fibers, particles and other desired absorbent core materials may be entrained in any suitable gaseous medium. In an embodiment, the absorbent composite 88 can have at least about 70% by weight of a superabsorbent material. In an embodiment, the absorbent composite 88 can have at least about 70 to about 100% by weight of a superabsorbent material.

As the forming surface 84 enters and then traverses through the forming chamber 54, the component materials of the absorbent composite 88, such as, the fibrous material, are operatively carried or transported by an entraining air stream that is drawn through the first web 82 and the forming surface 84. Typically, the low pressure, vacuum generating system is constructed and arranged to produce the desired airflow through the first web 82 and the forming surface 84. Such vacuum forming systems are well known in the art.

The stream of air-entrained absorbent materials 86 can pass through the forming chamber 54 for deposition onto the first web 82 which overlies the forming surface 84. The forming chamber 54 can serve to direct and concentrate the air-entrained absorbent materials 86, and to provide a desired velocity profile in the air-entrained stream of absorbent materials 86. Typically, the forming chamber 54 is supported by suitable structural members, which together form a support frame for the forming chamber. The frame may be anchored and/or joined to other suitable structural components, as necessary or desirable.

The forming surface 84 can be provided by any suitable mechanism. In the representatively shown configuration, the forming surface 84 is provided by a forming drum 66. Other conventional techniques for providing the forming surface 84 may also be employed. For example, the forming surface 84 may be provided by an endless forming belt.

In the representatively shown configuration, a forming drum system operatively provides the moving forming surface 84. More particularly, the moving foraminous forming surface 84 can be provided by an outer peripheral surface region of a rotatable forming drum 66. The forming drum 66 is rotatable in a selected direction of rotation, and can be rotated by employing a drum drive shaft that is operatively joined to any suitable drive mechanism (not shown). For example, the drive mechanism can include an electric or other motor which is directly or indirectly coupled to the drive shaft. While the shown arrangement provides a forming drum that is arranged to rotate in a counter-clockwise direction, it should be readily apparent that the forming drum may alternatively be arranged to rotate in a clockwise direction. A suitable forming drum and forming system are taught in U.S. Pat. No. 6,630,096 to Venturino et al. issued Oct. 7, 2003, the entirety of which is incorporated herein by reference to the extent that it is consistent herewith.

In the illustrated embodiment, under the influence of the vacuum generating source, a conveying air stream is drawn through the first web 82 and the foraminous forming surface 84 into the interior of the forming drum 66, and is subsequently passed out of the drum through the vacuum supply conduit 68. As the air-entrained absorbent materials 86 impinge on the first web 82, the air component is passed through the first web 82 and the forming surface 84 and the absorbent materials 86 are retained on the first web 82 to form a nonwoven unitary absorbent composite 88 thereon. The illustrated embodiments show a continuously formed unitary absorbent composite 88 formed on the first web 82. However, those skilled in the art will readily appreciate that discrete absorbent cores may alternatively be formed on the first web 82 such that a space exists between the absorbent cores. Therefore, where the term "absorbent composite" or "unitary absorbent composite" is used herein, the term "discrete absorbent core" or "discrete unitary absorbent core" is equally applicable in various embodiments. Suitable methods for forming discrete absorbent cores are disclosed in U.S. patent application Ser. No. 11/215,876 to Wisneski et al. entitled "Method and Apparatus for Making Absorbent Article With Core Wrap" and filed on Aug. 30, 2005, the entirety of which is incorporated herein by reference to the extent that it is consistent herewith.

Optionally, a scarfing system may be positioned at the exit region 58 of the forming chamber 54. The scarfing system can include a scarfing chamber 70 and a scarfing roll 72 which is positioned within the scarfing chamber. The scarfing roll can abrade excess absorbent material 86 from the absorbent composite 88, and the removed fibers can be transported away from the scarfing chamber 70 with a suitable discharge conduit, as is well known in the art. The removed absorbent material 86 may, for example, be recycled back into the forming chamber 54 or the fiberizer 60, as desired. Additionally, the scarfing roll can rearrange and redistribute the web material along the longitudinal machine-direction of the web and/or along the lateral cross-direction of the web.

The rotatable scarfing roll may be operatively connected and joined to a suitable shaft member, and may be driven by a suitable drive system (not shown). The scarfing roll system can provide a conventional trimming mechanism for removing or redistributing any excess, z-directional thickness of the absorbent composite 88 that has been deposited on the first web 82. The surface of the scarfing roll can be adjusted to provide a desired contour along the scarfed surface of the absorbent composite 88. The scarfing roll can, for example, be configured to provide a substantially flat surface along the scarfed surface of the absorbent composite 88. The scarfing roll can optionally be configured to provide a non-flat surface. The scarfing roll 72 is disposed in spaced adjacent relationship to the forming surface 84, and the forming surface 84 is translated past the scarfing roll. A conventional transporting mechanism, such as a suction fan (not shown) can draw the removed fibrous material away from the formed absorbent composite 88 and out from the scarfing chamber 70.

The scarfing roll 72 may be rotated in a direction which moves a contacting surface of the scarfing roll in a counter-direction that is opposite the movement direction of the absorbent composite 88. Alternatively, the scarfing roll 72 may be rotated in a co-direction that is the same as the movement direction of absorbent composite 88. In either situation, the rotational speed of the scarfing roll 72 should be suitably selected to provide an effective scarfing action against the contacted surface of the formed absorbent composite 88. In like manner, any other suitable trimming mechanism may be employed in place of the scarfing roll assembly to provide a cutting or abrading action to the laid fibrous web by a relative movement between the fibrous web and the selected trimming mechanism. A suitable scarfing system is taught in U.S. Pat. No. 6,627,130 to Kugler et al. issued Sep. 30, 2003, the entirety of which is incorporated herein by reference to the extent that it is consistent (i.e., not in conflict) herewith.

After formation of the absorbent composite 88, the second web 90 is overlaid upon the absorbent composite 88 and the first web 82 while both are conformed to the forming surface 84. The second web 90 is then joined to the first web 82 while still conformed to the forming surface 84 to form the completed absorbent composite web 88. Subsequently, with the rotation of the drum, the formed absorbent composite web 88 can be removed from the forming surface 84. The removal operation may be provided by the weight of the absorbent composite web 88, by centrifugal force, by a positive air pressure, or by combinations thereof. The positive air pressure can be produced, for example, by a source of compressed air or a fan which generates a pressurized air flow that exerts a force directed outwardly through the forming surface.

The portion of the forming surface 84 that is carrying the absorbent composite web 88 can be moved to an optional pressure blow-off zone of the forming drum system. In the blow-off zone, air can be introduced under pressure and directed radially outwardly against absorbent composite web 88 on the portion of the forming surface that becomes aligned with the blow-off zone. The gas pressure can effect a ready release of the absorbent composite web 88 from the forming surface 84, and the absorbent composite web 88 can be removed from the forming surface onto a suitable transport mechanism.

A web transporter can receive the absorbent composite web 88 from the forming drum 66, and convey the absorbent composite web 88 for further processing. In various embodiments, portions the absorbent composite web 88, such as the first web 82 and/or the second web 90, may be folded to seal the edges of the absorbent structure 94.

Suitable web transporters can, for example, include conveyer belts, vacuum drums, transport rollers, electromagnetic suspension conveyors, fluid suspension conveyors, or the like, as well as combinations thereof. As representatively shown, the web transporter can be provided by a system which includes the illustrated endless conveyor belt 74 disposed about rollers 76. In a particular configuration of the invention, a vacuum suction box 78 can be located below the conveyor belt 74 to help remove the absorbent composite web from the forming surface 84. The vacuum box 78 opens onto the belt 74, and a suction of air out of the vacuum box can draw an air flow through perforations in the conveyor belt. This flow of air can, in turn, operate to draw the absorbent composite web 88 away from the forming surface. The vacuum box can be employed with or without the use of a positive pressure in the blow-off zone.

On the forming surface 84, the absorbent composite web has very little integrity and requires stabilization. The absorbent composite 88 is advanced by the forming surface 84, and where desired, the absorbent composite first may be passed to a suitable first dispensing means 95, such as a spray nozzle, doctor blade, roller applicator, or the like, where an aqueous composite stabilizer is applied to the surface of the loose web. The vacuum applied beneath the first dispensing means 95 helps to draw the absorbent composite stabilizer into the web. The first dispensing means 95 or applicator is essentially coextensive with the width of the absorbent composite, and preferably a substantially uniform coating of the aqueous composite stabilizer is applied to the absorbent composite. However, the aqueous composite stabilizer may be applied as a non-uniform, random or pattern coating, and because the aqueous composite stabilizer is water-based, it will diffuse throughout the absorbent composite and function as a binder.

In some embodiments, the first dispensing means 95 includes at least one nozzle having an aperture for exhausting the aqueous composite stabilizer therefrom. In some embodiments, the nozzles include multiple gas apertures for exhausting gas therefrom. In a preferred embodiment, airless spray nozzles are utilized. The spray apparatus can comprise a nozzle assembly having a plurality of nozzles depositing aqueous composite stabilizer onto the surface of the absorbent core. The plurality of nozzles can define an array of nozzles extending across the width of the formed absorbent core, and can deposit aqueous composite stabilizer across a width, of the absorbent core.

In some embodiments, it is useful to target spray of the aqueous composite stabilizer to be about 5 mm inside the outer edge of the absorbent composite web. Spraying the absorbent composite stabilizer primarily in the center of the absorbent composite has minimal negative impact on overall pad stability testing, but significantly reduces over-spray issues. This may help reduce contamination of the apparatus from overspray and poor spray patterns.

The extent or degree of penetration of the aqueous composite stabilizer into the absorbent composite 88 may be controlled by controlling the amount of aqueous composite stabilizer applied and by controlling nozzle pressure and the vacuum applied to the absorbent composite 88 in that the vacuum helps to draw the aqueous composite stabilizer into the absorbent composite 88. It is optional to coat both surfaces of the absorbent composite with the aqueous composite stabilizer. Thus, the absorbent composite is advanced to a second dispensing means 96 where aqueous composite stabilizer is now applied to the opposite side forming a resultant absorbent structure 94 downstream from the forming system 42. In some desirable embodiments, only the second dispensing means 96 downstream from the forming system 42 is utilized.

Optionally, the absorbent structure may be formed with additional process steps in the forming system 42 if desired. For example, the absorbent structure can be optionally routed through a debulker (not shown) where it would be reduced in thickness. In addition, a pad cut-off (not-shown) may be utilized to severing or cutting the web of absorbent structures into individual and discrete absorbent structures. In some desirable embodiments, the second dispensing means 96 is located downstream of such additional components.

In an embodiment, the first and second dispensing means 95, 96 may include a single spray nozzle. In an embodiment, the first and second dispensing means 95, 96 may include more than one nozzle. One such embodiment will include three spray nozzles including a registration and pulsing system. In this embodiment, the center nozzle will continuously apply the aqueous absorbent composite to the center of the absorbent composite, and the outer nozzles will apply a pulsed amount aqueous absorbent composite to correspond to the ears or outer edges of the absorbent composite web. This allows for the formation of shaped absorbent structures.

After formation of the absorbent structure, the absorbent structure may be incorporated into an absorbent article. Various methods for constructing an absorbent article are described in U.S. patent application Ser. No. 14/062,278 filed Oct. 24, 2013 by Ruman et al.; U.S. patent application Ser. No. 14/068,918 filed Oct. 31, 2013 by Sina et al.; U.S. patent application Ser. No. 14/068,913 filed Oct. 31, 2013 by Bennett et al.; PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al., which are incorporated herein by reference.

The resulting absorbent structure web 94 still contains water but nonetheless exhibits sufficient integrity and can be rolled or cut into individual absorbent structures to be incorporated into an absorbent article without additional drying to remove the water because the absorbent composite stabilizer is present. One skilled in the art would expect to rely on a curing or heating step to achieve integrity for the absorbent composite once the aqueous composite stabilizer is applied. In addition, one skilled in the art would expect to completely dry the material to prevent mold from forming. The high percentage of superabsorbent material in the absorbent composite ensures drying and prevents mold formation.

Unexpectedly, application of aqueous composite stabilizer onto high superabsorbent concentration containing absorbent composites results in fast integrity development in the manufacturing process due to the fast absorption of water from the aqueous composite stabilizer by the superabsorbent. As the aqueous composite stabilizer is added to the surface of the absorbent composite, the stabilizing component of the aqueous composite stabilizer penetrates into and throughout the aqueous composite. The superabsorbent material in the absorbent composite absorbs the water in the aqueous composite stabilizer, leaving the stabilizing component to coat the fibers in the absorbent composite. This binds the fibers in the absorbent composite together, thereby providing the requisite integrity in the absorbent composite.

As the superabsorbent material absorbs the water in the aqueous composite stabilizer, a dry absorbent composite is formed. This dry absorbent composite can be incorporated into a product that is packaged without additional drying. Adding water to partially hydrate the superabsorbent material does not significantly affect the ability of the absorbent core to absorb more aqueous liquid. Typically, superabsorbent material is already between about 5% to about 10% hydrated when put into absorbent articles. By adding an aqueous composite stabilizer, the absorbent composite may be from between about 5% to about 80% hydrated. However, this level of hydration does not prevent the absorbent core from absorbing liquids. Superabsorbent material is designed to hold enough liquid to be from about 1000% to about 4000% hydrated when fully hydrated. Thus, the addition of an aqueous composite stabilizer works to provide integrity without hindering the absorbent capacity of the product.

As discussed above, no additional drying capabilities are required as the superabsorbent material in the high superabsorbent material composites absorbs the aqueous portion of the aqueous composite stabilizer. This drying mechanism places aqueous composite stabilizer at the surface of the superabsorbent material and fibers, providing the bonding required for integrity generation required. In addition to high process integrity and product integrity, the introduction of aqueous composite stabilizer to the absorbent composite provides additional product improvements: the integrity from the aqueous composite stabilizer eliminates the need to emboss the composite to achieve integrity, a process that damages the superabsorbent material in the composite, reducing fluid performance.

In addition, when the water from the aqueous composite stabilizer is absorbed by the superabsorbent material, it softens the superabsorbent material. This reduces the gritty, grainy feel of a high superabsorbent material containing core. Also, since the debulking step can be eliminated in the aqueous composite stabilizer process, hard spots in an absorbent composite are eliminated. Since the superabsorbent material is immobilized by the aqueous composite stabilizer, gel-on-skin issues are also greatly reduced. In addition, the absorbent structure is not cured to impart integrity to the structure.

Finally, the spray application of aqueous composite stabilizer in the manufacturing process provides a fully sealed wrapped composite, eliminating the need to end seal the composite. Taken wholly, an overall improved product is realized.

Figure 3:
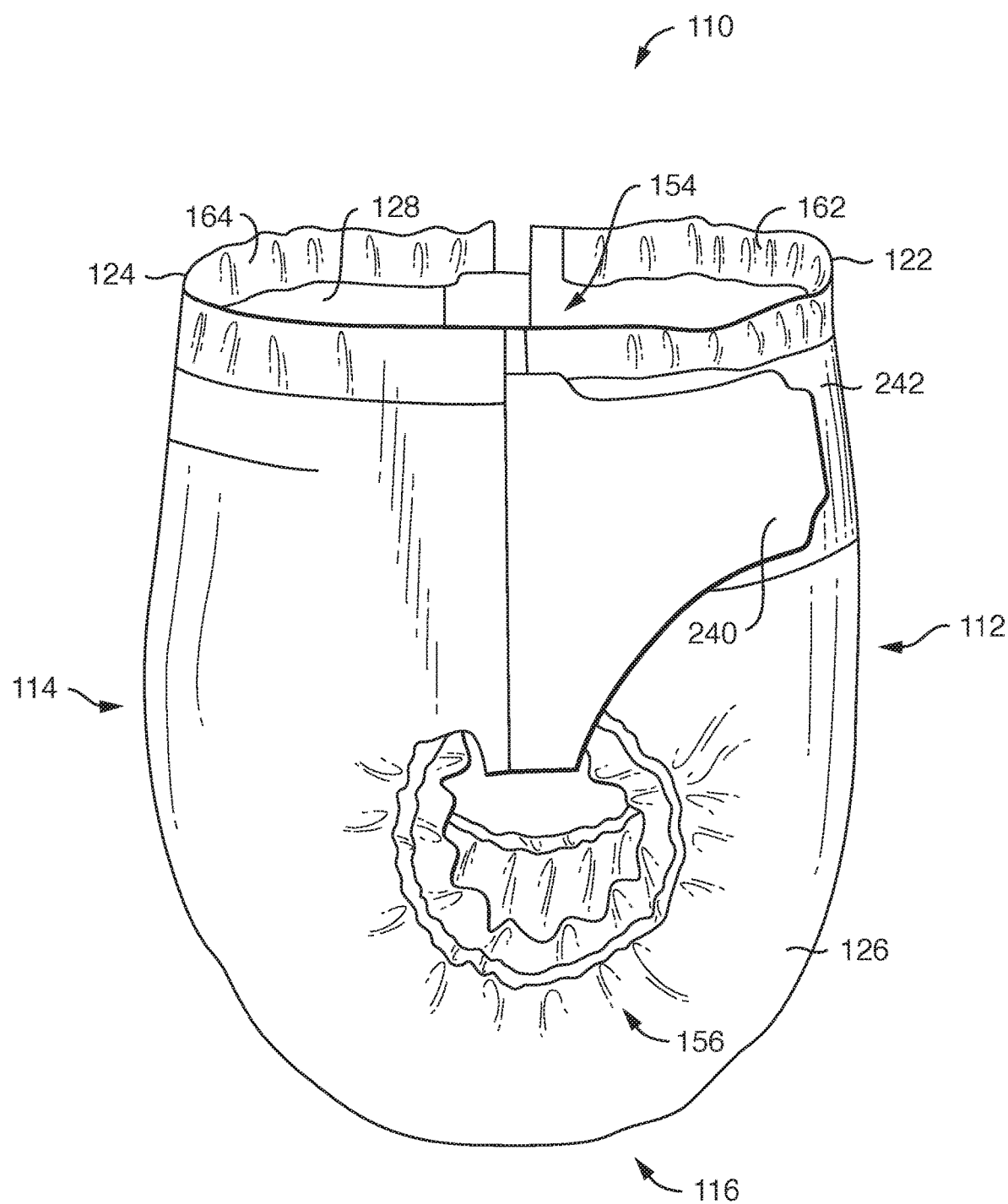
FIG. 3 is a side view illustration of an embodiment of an absorbent article.

Referring to FIG. 3, a disposable absorbent article 110 of the present disclosure is exemplified in the form of a diaper. It is to be understood that the present disclosure is suitable for use with various other personal care absorbent articles, such as, for example, feminine hygiene products, adult incontinence products and pads, without departing from the scope of the present disclosure. While the embodiments and illustrations described herein may generally apply to absorbent articles manufactured in the product longitudinal direction, which is hereinafter called the machine direction manufacturing of a product, it should be noted that one of ordinary skill could apply the information herein to absorbent articles manufactured in the latitudinal direction of the product which hereinafter is called the cross direction manufacturing of a product without departing from the spirit and scope of the disclosure. The absorbent article 110 illustrated in FIG. 3 includes a front waist region 112, a back waist region 114, and a crotch region 116 interconnecting the front and back waist regions, 112 and 114, respectively. The absorbent article 110 has a pair of longitudinal side edges, 112 and 114 (shown in FIG. 4), and a pair of opposite waist edges, respectively designated front waist edge 122 and back waist edge 124. The front waist region 112 can be contiguous with the front waist edge 122 and the back waist region 114 can be contiguous with the back waist edge 124.

Figure 4:
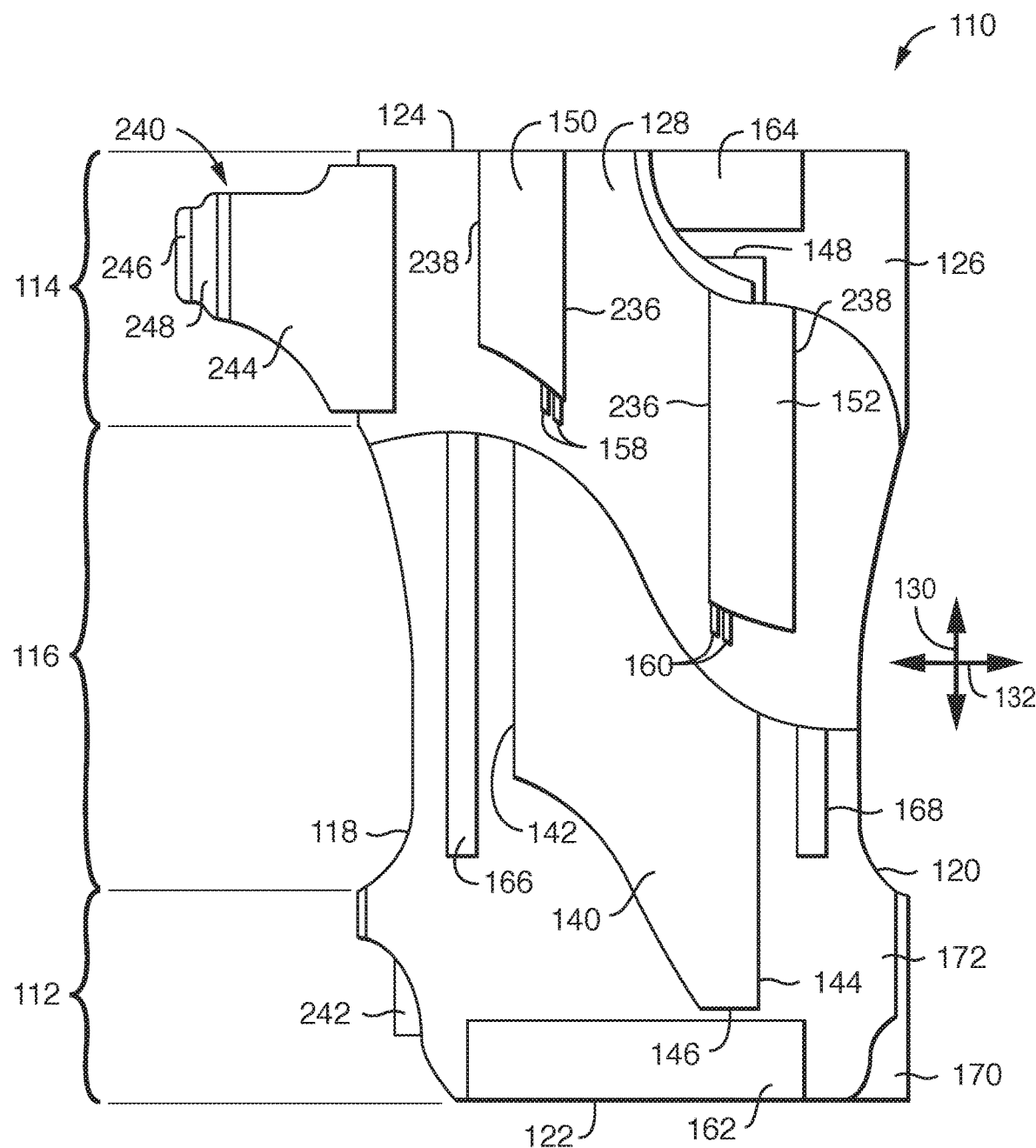
FIG. 4 is a top down view of an embodiment of an absorbent article with portions cut away for clarity.

Referring to FIG. 4, a non-limiting illustration of an absorbent article 110, such as, for example, a diaper, is illustrated in a top down view with portions cut away for clarity of illustration. The absorbent article 110 can include an outer cover 126 and a body facing material 128. In an embodiment, the body facing material 128 can be bonded to the outer cover 126 in a superposed relation by any suitable means such as, but not limited to, adhesives, ultrasonic bonds, thermal bonds, pressure bonds, or other conventional techniques. The outer cover 126 can define a length, or longitudinal direction 130, and a width, or lateral direction 132, which, in the illustrated embodiment, can coincide with the length and width of the absorbent article 110. The longitudinal direction 130 and the lateral direction 132 of the absorbent article 110, and of the materials which form the absorbent article 110, can provide the X-Y planes, respectively, of the absorbent article 110 and of the materials which form the absorbent article 110. The absorbent article 110, and the materials which form the absorbent article 110, can also have a Z-direction. A measurement, taken under pressure, in the Z-direction of a material which forms the absorbent article 110 can provide a measurement of the thickness of the material. A measurement, taken under pressure, in the Z-direction of the absorbent article 110 can provide a measurement of the bulk of the absorbent article 110.

Referring to FIGS. 3-8, an absorbent body 140 can be disposed between the outer cover 126 and the body facing material 128. The absorbent body 140 can have longitudinal edges, 142 and 144, which, in an embodiment, can form portions of the longitudinal side edges, 118 and 120, respectively, of the absorbent article 110 and can have opposite end edges, 146 and 148, which, in an embodiment, can form portions of the waist edges, 122 and 124, respectively, of the absorbent article 110. In an embodiment, the absorbent body 140 can have a length and width that are the same as or less than the length and width of the absorbent article 110. In an embodiment, a pair of containment flaps, 150 and 152, can be present and can inhibit the lateral flow of body exudates.

The front waist region 112 can include the portion of the absorbent article 110 that, when worn, is positioned at least in part on the front of the wearer while the back waist region 114 can include the portion of the absorbent article 110 that, when worn, is positioned at least in part on the back of the wearer. The crotch region 116 of the absorbent article 110 can include the portion of the absorbent article 110, that, when worn, is positioned between the legs of the wearer and can partially cover the lower torso of the wearer. The waist edges, 122 and 124, of the absorbent article 110 are configured to encircle the waist of the wearer and together define the central waist opening 154 (such as shown in FIG. 3). Portions of the longitudinal side edges, 118 and 120, in the crotch region 116 can generally define leg openings 156 (such as shown in FIG. 3) when the absorbent article 110 is worn.

The absorbent article 110 can be configured to contain and/or absorb liquid, solid, and semi-solid body exudates discharged from the wearer. For example, containment flaps, 150 and 152, can be configured to provide a barrier to the lateral flow of body exudates. A flap elastic member, 158 and 160, can be operatively joined to each containment flap, 150 and 152, in any suitable manner known in the art. The elasticized containment flaps, 150 and 152, can define a partially unattached edge that can assume an upright configuration in at least the crotch region 116 of the absorbent article 110 to form a seal against the wearer's body. The containment flaps, 150 and 152, can be located along the absorbent article 110 longitudinal side edges, 118 and 120, and can extend longitudinally along the entire length of absorbent article 110 or can extend partially along the length of the absorbent article 110. Suitable construction and arrangements for containment flaps, 150 and 152, are generally well known to those skilled in the art and are described in U.S. Pat. No. 4,704,116 issued Nov. 3, 1987, to Enloe and U.S. Pat. No. 5,562,650 issued Oct. 8, 1996 to Everett et al., which are incorporated herein by reference.

To further enhance containment and/or absorption of body exudates, the absorbent article 110 can suitably include a front waist elastic member 162, a rear waist elastic member 164, and leg elastic members, 166 and 168, as are known to those skilled in the art. The waist elastic members, 162 and 164, can be attached to the outer cover 126, the body facing material 128 along the opposite waist edges, 122 and 124, and can extend over part or all of the waist edges, 122 and 124. The leg elastic members, 166 and 168, can be attached to the outer cover 126, the body facing material 128 along the opposite longitudinal side edges, 118 and 120, and positioned in the crotch region 116 of the absorbent article 110.

Additional details regarding each of these elements of the absorbent article 110 described herein can be found below and with reference to the Figures.

Outer Cover:

The outer cover 126 can be breathable and/or liquid impermeable. The outer cover 126 can be elastic, stretchable or non-stretchable. The outer cover 126 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 126 can be constructed of a microporous polymeric film, such as polyethylene or polypropylene.

In an embodiment, the outer cover 126 can be a single layer of a liquid impermeable material. In an embodiment, the outer cover 126 can be suitably stretchable, and more suitably elastic, in at least the lateral or circumferential direction 132 of the absorbent article 110. In an embodiment, the outer cover 126 can be stretchable, and more suitably elastic, in both the lateral 132 and the longitudinal 130 directions. In an embodiment, the outer cover 126 can be a multi-layered laminate in which at least one of the layers is liquid impermeable. In an embodiment such as illustrated in FIGS. 5-8, the outer cover 126 may be a two layer construction, including an outer layer 170 material and an inner layer 172 material which can be bonded together such as by a laminate adhesive. Suitable laminate adhesives can be applied continuously or intermittently as beads, a spray, parallel swirls, or the like. Suitable adhesives can be obtained from Bostik Findlay Adhesives, Inc. of Wauwatosa, Wis., U.S.A. It is to be understood that the inner layer 172 can be bonded to the outer layer 170 utilizing ultrasonic bonds, thermal bonds, pressure bonds, or the like.

The outer layer 170 of the outer cover 126 can be any suitable material and may be one that provides a generally cloth-like texture or appearance to the wearer. An example of such material can be a 100% polypropylene bonded-carded web with a diamond bond pattern available from Sandler A. G., Germany, such as 30 gsm Sawabond 4185® or equivalent. Another example of material suitable for use as an outer layer 170 of an outer cover 126 can be a 20 gsm spunbond polypropylene non-woven web.

The liquid impermeable inner layer 172 of the outer cover 126 (or the liquid impermeable outer cover 126 where the outer cover 126 is of a single-layer construction) can be either vapor permeable (i.e., "breathable") or vapor impermeable. The liquid impermeable inner layer 172 (or the liquid impermeable outer cover 126 where the outer cover 126 is of a single-layer construction) may be manufactured from a thin plastic film, although other liquid impermeable materials may also be used. The liquid impermeable inner layer 172 (or the liquid impermeable outer cover 126 where the outer cover 126 is of a single-layer construction) can inhibit liquid body exudates from leaking out of the absorbent article 110 and wetting articles, such as bed sheets and clothing, as well as the wearer and caregiver. An example of a material for a liquid impermeable inner layer 172 (or the liquid impermeable outer cover 126 where the outer cover 126 is of a single-layer construction) can be a printed 19 gsm Berry Plastics XP-8695H film or equivalent commercially available from Berry Plastics Corporation, Evansville, Ind., U.S.A.

Where the outer cover 126 is of a single layer construction, it can be embossed and/or matte finished to provide a more cloth-like texture or appearance. The outer cover 126 can permit vapors to escape from the absorbent article 110 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 140 can be superposed over the inner layer 172 of the outer cover 126, extending laterally between the leg elastic members, 166 and 168, and can be bonded to the inner layer 172 of the outer cover 126, such as by being bonded thereto with adhesive. However, it is to be understood that the absorbent body 140 may be in contact with, and not bonded with, the outer cover 126 and remain within the scope of this disclosure. In an embodiment, the outer cover 126 can be composed of a single layer and the absorbent body 140 can be in contact with the single layer of the outer cover 126. In an embodiment, a layer, such as but not limited to, a core wrap layer 178, can be positioned between the absorbent body 140 and the outer cover 126.

Core Wrap Layer:

In various embodiments, such as illustrated in the non-limiting example of FIG. 5, an absorbent article 110 can be constructed without a core wrap layer 178. In various embodiments, such as illustrated in the non-limiting examples of FIGS. 6-8, the absorbent article 110 can have a core wrap layer 178. The core wrap layer 178 can have a wearer facing surface 174 and a garment facing surface 176. In an embodiment, the core wrap layer 178 can be in contact with the absorbent body 140. In an embodiment, the core wrap layer 178 can be bonded to the absorbent body 140. Bonding of the core wrap layer 178 to the absorbent body 140 can occur via any means known to one of ordinary skill, such as, but not limited to, adhesives. In an embodiment, such as illustrated in the non-limiting example of FIG. 6, a core wrap layer 178 can be positioned between the body facing material 128 and the absorbent core 140. In an embodiment, such as illustrated in the non-limiting example of FIG. 7, a core wrap layer 178 can completely encompass the absorbent body 140 and can be sealed to itself. In such an embodiment, the core wrap layer 178 may be folded over on itself and then sealed using, for example, heat, adhesive and/or pressure. In an embodiment, such as, for example, in the non-limiting illustration of FIG. 8, a core wrap layer 178 may be composed of separate sheets of material which can be utilized to partially or fully encompass the absorbent body 140 and which can be sealed together using a sealing means such as an ultrasonic bonder or other thermochemical bonding means or the use of an adhesive. In another embodiment, there is no core wrap layer at all. In other embodiments, the core wrap layer can be on only one of the wearer facing surface 174 and a garment facing surface 176. Due the nature of the absorbent structure defined herein, the core wrap may not be included on the wearer facing surface due to the increased integrity of absorbent structure resulting in less gel on skin issues. Due the nature of the absorbent structure defined herein, the core wrap may not be included on the garment facing surface, due to the absorbent structure swelling and removing soft edges.

In an embodiment, the core wrap layer 178 can be in contact with and/or bonded with the wearer facing surface 174 of the absorbent body 140. In an embodiment, the core wrap layer 178 can be in contact with and/or bonded with the wearer facing surface 174 and at least one of the edges, 142, 144, 146 and/or 148, of the absorbent body 140. In an embodiment, the core wrap layer 178 can be in contact with and/or bonded with the wearer facing surface 174, at least one of the edges, 142, 144, 146 and/or 148, and the garment facing surface 176 of the absorbent body 140. In an embodiment, the absorbent body 140 may be partially or completely encompassed by a core wrap layer 178.

The core wrap layer 178 can be pliable, less hydrophilic than the absorbent body 140, and sufficiently porous to thereby permit liquid body exudates to penetrate through the core wrap layer 178 to reach the absorbent body 140. In an embodiment, the core wrap layer 178 can have sufficient structural integrity to withstand wetting thereof and of the absorbent composite. In an embodiment, the core wrap layer 178 can be constructed from a single layer of material or it may be a laminate constructed from two or more layers of material.

In an embodiment, the core wrap layer 178 can include, but is not limited to, natural and synthetic fibers such as, but not limited to, polyester, polypropylene, acetate, nylon, polymeric materials, cellulosic materials such as wood pulp, cotton, rayon, viscose, LYOCELL® such as from Lenzing Company of Austria, or mixtures of these or other cellulosic fibers, and combinations thereof. Natural fibers can include, but are not limited to, wool, cotton, flax, hemp, and wood pulp.

In various embodiments, the core wrap layer selected from metlblown-spunbond-meltblown fabric, spunbond fabric, meltblown fabric, coform fabric, carded web, bonded-carded web, bicomponent spunbond fabric, spunlace, tissue, and combinations thereof.

In various embodiments, the core wrap layer 178 can include cellulosic material. In various embodiments, the core wrap layer 178 can be creped wadding or a high-strength tissue. In various embodiments, the core wrap layer 178 can include polymeric material. In an embodiment, a core wrap layer 178 can include a spunbond material. In an embodiment, a core wrap layer 178 can include a meltblown material. In an embodiment, the core wrap layer 178 can be a laminate of a meltblown nonwoven material having fine fibers laminated to at least one spunbond nonwoven material layer having coarse fibers. In such an embodiment, the core wrap layer 178 can be a spunbond-meltblown ("SM") material. In an embodiment, the core wrap layer 178 can be a spunbond-meltblown-spunbond ("SMS") material. A non-limiting example of such a core wrap layer 178 can be a 10 gsm spunbond-meltblown-spunbond material. In various embodiments, the core wrap layer 178 can be composed of at least one material which has been hydraulically entangled into a nonwoven substrate. In various embodiments, the core wrap layer 178 can be composed of at least two materials which have been hydraulically entangled into a nonwoven substrate. In various embodiments, the core wrap layer 178 can have at least three materials which have been hydraulically entangled into a nonwoven substrate. A non-limiting example of a core wrap layer 178 can be a 33 gsm hydraulically entangled substrate. In such an example, the core wrap layer 178 can be a 33 gsm hydraulically entangled substrate composed of a 12 gsm spunbond material, a 10 gsm wood pulp material having a length from about 0.6 cm to about 5.5 cm, and an 11 gsm polyester staple fiber material. To manufacture the core wrap layer 178 just described, the 12 gsm spunbond material can provide a base layer while the 10 gsm wood pulp material and the 11 gsm polyester staple fiber material can be homogeneously mixed together and deposited onto the spunbond material and then hydraulically entangled with the spunbond material.

In various embodiments, a wet strength agent can be included in the core wrap layer 178. A non-limiting example of a wet strength agent can be Kymene 6500 (557LK) or equivalent available from Ashland Inc. of Ashland, Ky., U.S.A. In various embodiments, a surfactant can be included in the core wrap layer 178. In various embodiments, the core wrap layer 178 can be hydrophilic. In various embodiments, the core wrap layer 178 can be hydrophobic and can be treated in any manner known in the art to be made hydrophilic.

In an embodiment, the core wrap layer 178 can be in contact with and/or bonded with an absorbent composite which is made at least partially of particulate material such as superabsorbent material. In an embodiment in which the core wrap layer 178 at least partially or completely encompasses the absorbent body 140.

In an embodiment, the core wrap layer 178 may have a longitudinal length the same as, greater than, or less than the longitudinal length of the absorbent composite 140. The core wrap layer 178 can have a longitudinal length ranging from about 150 to about 520 mm.

Acquisition Layer:

In various embodiments, such as illustrated, for example, in FIG. 7, the absorbent article 10 can have an acquisition layer 184. The acquisition layer 184 can help decelerate and diffuse surges or gushes of liquid body exudates penetrating the body facing material 128. In an embodiment, the acquisition layer 184 can be positioned between the body facing material 128 and the absorbent body 140 to take in and distribute body exudates for absorption by the absorbent body 140. In an embodiment, the acquisition layer 184 can be positioned between the body facing material 128 and a core wrap layer 178 if a core wrap layer 178 is present.

The acquisition layer 184 can have a wearer facing surface 186 and a garment facing surface 188. In an embodiment, the acquisition layer 184 can be in contact with and/or bonded with the body facing material 128. In an embodiment in which the acquisition layer 184 is bonded with the body facing material 128, bonding of the acquisition layer 184 to the body facing material 128 can occur through the use of an adhesive and/or point fusion bonding. The point fusion bonding can be selected from, but is not limited to, ultrasonic bonding, pressure bonding, thermal bonding, and combinations thereof. In an embodiment, the point fusion bonding can be provided in any pattern as deemed suitable.

The acquisition layer 184 may have any longitudinal length dimension as deemed suitable. In an embodiment, the acquisition layer 184 can have any length such that the acquisition layer 184 can be coterminous with the waist edges, 122 and 124, of the absorbent article 110.

In an embodiment, the longitudinal length of the acquisition layer 184 can be the same as the longitudinal length of the absorbent body 140. In such an embodiment the midpoint of the longitudinal length of the acquisition layer 184 can substantially align with the midpoint of the longitudinal length of the absorbent body 140.

In an embodiment, the longitudinal length of the acquisition layer 184 can be shorter than the longitudinal length of the absorbent body 140. In such an embodiment, the acquisition layer 184 may be positioned at any desired location along the longitudinal length of the absorbent body 140. As an example of such an embodiment, the absorbent article 110 may contain a target area where repeated liquid surges typically occur in the absorbent article 110. The particular location of a target area can vary depending on the age and gender of the wearer of the absorbent article 110 and design of the absorbent article 110. For example, males tend to urinate further toward the front region of the absorbent article 110 and the target area may be phased forward within the absorbent article 110. For example, the target area for a male wearer may be positioned about 70 mm forward of the longitudinal midpoint of the absorbent composite. The female target area can be located closer to the center of the crotch region 116 of the absorbent article 110. For example, the target area for a female wearer may be positioned about 26 mm forward of the longitudinal midpoint of the absorbent body 140. As a result, the relative longitudinal placement of the acquisition layer 184 within the absorbent article 110 can be selected to best correspond with the target area of either or both categories of wearers.

In an embodiment, the acquisition layer 184 can have a size dimension that is the same size dimension as the target area of the absorbent article 110 or a size dimension greater than the size dimension of the target area of the absorbent article 110. In an embodiment, the acquisition layer 184 can be in contact with and/or bonded with the body facing material 128 at least partially in the target area of the absorbent article 110.

In various embodiments, the acquisition layer 184 can have a longitudinal length shorter than, the same as or longer than the longitudinal length of the absorbent body 140. In an embodiment in which the absorbent article 110 is a diaper, the acquisition layer 184 may have a longitudinal length from about 120 to about 320 mm. In such an embodiment, the acquisition layer 184 may be shorter in longitudinal length than the longitudinal length of the absorbent body 140 and may be phased from the front end edge 146 of the absorbent body 140 a distance of from about 15 mm to about 40 mm. In an embodiment in which the absorbent article 110 may be a training pant or youth pant, the acquisition layer 184 may have a longitudinal length from about 120 to about 520 mm. In such an embodiment, the acquisition layer 184 may have a longitudinal length shorter than the longitudinal length of the absorbent body 140 and may be phased a distance of from about 25 mm to about 85 mm from the front end edge 146 of the absorbent composite 140. In an embodiment in which the absorbent article 110 is an adult incontinence garment, the acquisition layer 184 may have a longitudinal length from about 200 mm to about 450 mm. In such an embodiment, the acquisition layer 184 may have a longitudinal length shorter than the longitudinal length of the absorbent body 140 and the acquisition layer 184 may be phased a distance of from about 20 mm to about 75 mm from the front end edge 146 of the absorbent body 140.

The acquisition layer 184 may have any width as desired. The acquisition layer 184 may have a width dimension from about 15 mm to about 180 mm. The width of the acquisition layer 184 may vary dependent upon the size and shape of the absorbent article 110 within which the acquisition layer 184 will be placed. The acquisition layer 184 can have a width smaller than, the same as, or larger than the width of the absorbent body 140. Within the crotch region 116 of the absorbent article 110, the acquisition layer 184 can have a width smaller than, the same as, or larger than the width of the absorbent body 140.

In an embodiment, the acquisition layer 184 can include natural fibers, synthetic fibers, superabsorbent material, woven material, nonwoven material, wet-laid fibrous webs, a substantially unbounded airlaid fibrous web, an operatively bonded, stabilized-airlaid fibrous web, or the like, as well as combinations thereof. In an embodiment, the acquisition layer 184 can be formed from a material that is substantially hydrophobic, such as a nonwoven web composed of polypropylene, polyethylene, polyester, and the like, and combinations thereof.

In various embodiments, the acquisition layer 184 can have fibers which can have a denier of greater than about 5. In various embodiments, the acquisition layer 184 can have fibers which can have a denier of less than about 5. In various embodiments, the fluid acquisition layer selected from meltblown-spunbond-meltblown fabric, spunbond fabric, meltblown fabric, coform fabric, carded web, bonded-carded web, bicomponent spunbond fabric, spunlace, tissue, and combinations thereof In an embodiment, the acquisition layer 184 can be a through-air bonded-carded web such as a 50 gsm through-air bonded-carded web composite having a homogenous blend of about 50% sheath/core bicomponent polyethylene/polypropylene fibers having a fiber diameter of 3 denier and about 50% sheath/core bicomponent polyethylene/polypropylene fibers having a fiber diameter of 1.5 denier. An example of such a composite is a composite having about 50% ES FiberVisions 3 denier ESC-233 bicomponent fibers and about 50% ES FiberVisions 1.5 denier ESC-215 bicomponent fibers, or equivalent composite, available from ES FiberVisions Corp., Duluth, Ga., U.S.A.

In an embodiment, the acquisition layer 184 can be a through-air bonded-carded web such as a 50 gsm through-air bonded-carded web composite having a homogenous blend of about 50% Rayon fibers having a fiber diameter of 3 denier and about 50% sheath/core bicomponent polyethylene/polypropylene fibers having a fiber diameter of 1.5 denier. An example of such a composite is a composite having about 50% Kelheim 3 denier Rayon Galaxy fibers and about 50% ES FiberVisions 1.5 denier ESC-215 bicomponent fibers, or equivalent composite, available from ES FiberVisions Corp., Duluth, Ga., U.S.A.

In an embodiment, the acquisition layer 184 can be a through-air bonded-carded web such as a 35 gsm through-air bonded-carded web composite having a homogenous mixture of about 35% sheath/core bicomponent polyethylene/polypropylene fibers having a fiber diameter of 6 denier, about 35% sheath/core bicomponent polyethylene/polypropylene fibers having a fiber diameter of 2 denier, and about 30% polyester fibers having a fiber diameter of 6 denier. An example of such a composite is a composite having about 35% Huvis 180-N(PE/PP 6d), about 35% Huvis N-215 (PE/PP 2d), and about 30% Huvis SD-10 PET 6d, or equivalent composite, available from SamBo Company, Ltd, Korea.

In an embodiment, the acquisition layer 184 can be a thermally bonded, stabilized-airlaid fibrous web (e.g. Concert product code DT200.100.D0001) which is available from Glatfelter, a business having offices located in York, Pa., U.S.A.

Containment Flaps:

In an embodiment, containment flaps, 150 and 152, can be secured to the body facing material 128 of the absorbent article 110 in a generally parallel, spaced relation with each other laterally inward of the leg openings 156 to provide a barrier against the flow of body exudates to the leg openings 156. In an embodiment, the containment flaps, 150 and 152, can extend longitudinally from the front waist region 112 of the absorbent article 110, through the crotch region 116 to the back waist region 114 of the absorbent article 110. The containment flaps, 150 and 152, can be bonded to the body facing material by a seam of adhesive 237 to define a fixed proximal end 238 of the containment flaps, 150 and 152.

The containment flaps, 150 and 152, can be constructed of a fibrous material which can be similar to the material forming the body facing material 128. Other conventional material, such as polymer films, can also be employed. Each containment flap, 150 and 152, can have a moveable distal end 236 which can include flap elastics, such as flap elastics 158 and 160, respectively. Suitable elastic materials for the flap elastic, 158 and 160, can include sheets, strands or ribbons of natural rubber, synthetic rubber, or thermoplastic elastomeric materials.

The flap elastics, 158 and 160, as illustrated, can have two strands of elastomeric material extending longitudinally along the distal ends 236 of the containment flaps, 150 and 152, in generally parallel, spaced relation with each other. The elastic strands can be within the containment flaps, 150 and 152, while in an elastically contractible condition such that contraction of the strands gathers and shortens the distal ends 236 of the containment flaps, 150 and 152. As a result, the elastic strands can bias the distal ends 236 of each containment flap, 150 and 152, toward a position spaced from the proximal end 238 of the containment flaps, 150 and 152, so that the containment flaps, 150 and 152, can extend away from the body facing material 128 in a generally upright orientation of the containment flaps, 150 and 152, especially in the crotch region 116 of the absorbent article 110, when the absorbent article 110 is fitted on the wearer. The distal end 236 of the containment flaps, 150 and 152, can be connected to the flap elastics, 158 and 160, by partially doubling the containment flap, 150 and 152, material back upon itself by an amount which can be sufficient to enclose the flap elastics, 158 and 160. It is to be understood, however, that the containment flaps, 150 and 152, can have any number of strands of elastomeric material and may also be omitted from the absorbent article 110 without departing from the scope of this disclosure.

Leg Elastics:

Leg elastic members, 166 and 168, can be secured between the outer and inner layers, 170 and 172, respectively, of the outer cover 126, such as by being bonded therebetween by laminate adhesive, generally adjacent the lateral outer edges of the inner layer 172 of the outer cover 126. Alternatively, the leg elastic members, 166 and 168, may be disposed between other layers of the absorbent article 110. A wide variety of elastic materials may be used for the leg elastic members, 166 and 168. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate.

Fastening System:

In an embodiment, the absorbent article 110 can include a fastener system. The fastener system can include one or more back fasteners 240 and one or more front fasteners 242. Portions of the fastener system may be included in the front waist region 112, back waist region 114, or both. The fastener system can be configured to secure the absorbent article 110 about the waist of the wearer and maintain the absorbent article 110 in place during use. In an embodiment, the back fasteners 240 can include one or more materials bonded together to form a composite ear as is known in the art. For example, the composite fastener may be composed of a stretch component 244, a nonwoven carrier or hook base 246, and a fastening component 248.

Waist Elastic Members:

In an embodiment, the absorbent article 110 can have waist elastic members, 162 and 164, which can be formed of any suitable elastic material. In such an embodiment, suitable elastic materials can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. It is to be understood, however, that the waist elastic members, 162 and 164, may be omitted from the absorbent article 110 without departing from the scope of this disclosure.

The absorbent structure 140 can be superposed over the inner layer 172 of the outer cover 126, extending laterally between the leg elastic members, 166 and 168, and can be bonded to the inner layer 172 of the outer cover 126, such as by being bonded thereto with adhesive. However, it is to be understood that the absorbent structure 140 may be in contact with, and not bonded with, the outer cover 126 and remain within the scope of this disclosure. In an embodiment, the outer cover 126 can be composed of a single layer and the absorbent body 140 can be in contact with the single layer of the outer cover 126. In an embodiment, a layer, such as but not limited to, a core wrap layer 178, can be positioned between the absorbent body 140 and the outer cover 126.

EXAMPLE

An absorbent core was constructed as described in FIG. 2 above by forming the absorbent structure onto a first web of a spunbond-meltblown-spunbond nonwoven web. The absorbent structure was formed utilizing a mixture of 80% superabsorbent material and 20% pulp fiber. The superabsorbent material used in the absorbent structure was FAVOR SXM-9500 available from Evonik Industries, Greensboro, N.C. The pulp fiber used in the superabsorbent structure was NB-416 southern softwood pulpsheet available from Weyerhaeuser Co. of Federal Way, Wash.

After formation of the absorbent composite, an aqueous composite stabilizer having about 15.5% solids of the stabilizing component was applied to the absorbent composite utilizing both the first and second dispensing means to apply to both sides of the composite at an add-on rate of 2% by weight of the absorbent composite. The aqueous composite stabilizer included VINNAPAS® EZ 123 commercially available from Wacker Chemie AG, Munich, Del. as the stabilizing component. A second web of a spunbond-meltblown-spunbond nonwoven web was applied over the absorbent composite.

The first and second web was sealed together and the absorbent structure was cut into discrete absorbent cores. The resulting absorbent core was found to have sufficient absorbency and integrity for further processing and placement into an absorbent article.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. An absorbent article comprising:
   a topsheet,
   a backsheet, and
   an absorbent core formed by:
      forming an absorbent structure on a forming surface, the absorbent structure comprising at least about 70% by weight of a superabsorbent material, and
      applying an aqueous composite stabilizer to at least a first side of the absorbent structure, wherein the aqueous composite stabilizer comprises a stabilizing component, the stabilizing component being applied to the absorbent structure at an add-on rate of between about 1% and about 4% by weight of the absorbent structure and wherein the absorbent composite absorbs the water from the aqueous composite stabilizer.

2. The article of claim 1 wherein the stabilizing component is applied at an add-on rate of between about 1% and about 4% by weight of the absorbent structure.

3. The article of claim 1 wherein the stabilizing component is applied at an add-on rate of between about 1.5% and about 2.5% by weight of the absorbent structure.

4. The article of claim 1 wherein the aqueous composite stabilizer comprises from about 7.5% to about 55% by weight solids.

5. The article of claim 1 wherein the aqueous composite stabilizer comprises from about 11.5% to about 15.5% by weight solids.

6. The article of claim 1 wherein the absorbent structure has a basis weight of between 200 and 1000 grams per square meter.

7. The article of claim 1 wherein the forming surface is a fluid acquisition layer selected from metlblown-spunbond-meltblown, spunbond fabric, meltblown fabric, coform fabric, carded web, bonded-carded web, bicomponent spunbond fabric, spunlace, tissue, and combinations thereof.

8. The article of claim 1 further comprising forming the absorbent core without curing the absorbent structure.

9. The article of claim 1 wherein applying aqueous composite stabilizer comprises applying aqueous composite stabilizer to the absorbent structure no closer than 5 mm to an outer edge of the absorbent structure.

10. The article of claim 1 wherein application of the aqueous composite stabilizer further comprises applying with at least three spray nozzles, wherein a center nozzle will continuously apply the aqueous composite stabilizer to the center of the absorbent composite, and outer nozzles will apply aqueous composite stabilizer in a pulsed manner to correspond to outer edges of the absorbent structure.

11. The article of claim 1 further comprising application of the aqueous composite stabilizer to a second side of the absorbent structure.

12. The method article of claim 11 wherein application of the aqueous composite stabilizer on both a first side and a second side further comprises applying with at least three spray nozzles, wherein a center nozzle will continuously apply the aqueous composite stabilizer to the center of the absorbent structure, and outer nozzles will apply the aqueous composite stabilizer in a pulsed manner to correspond to outer edges of the absorbent structure.

13. The article of claim 1 wherein application of the aqueous composite stabilizer is done with a vacuum between about 1 to about 50 inches of water.

* * * * *